(12) United States Patent
Starobinets et al.

(10) Patent No.: US 12,283,360 B2
(45) Date of Patent: Apr. 22, 2025

(54) AUTOMATED SYSTEM FOR ERROR CHECKING INJECTION PARAMETERS DURING IMAGING EXAMS

(71) Applicant: KONINKLIJKE PHILIPS N.V., Eindhoven (NL)

(72) Inventors: Olga Starobinets, Newton, MA (US); Sandeep Madhukar Dalal, Winchester, MA (US); Ranjith Naveen Tellis, Tewksbury, MA (US); Hareesh Chamarthi, Cambridge, MA (US); Yuchen Qian, Lexington, MA (US); Vijay Parthasarathy, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 933 days.

(21) Appl. No.: 17/097,344

(22) Filed: Nov. 13, 2020

(65) Prior Publication Data
US 2021/0158946 A1  May 27, 2021

Related U.S. Application Data

(60) Provisional application No. 62/938,443, filed on Nov. 21, 2019.

(51) Int. Cl.
*G16H 20/17*   (2018.01)
*A61M 5/00*   (2006.01)
(Continued)

(52) U.S. Cl.
CPC ............ *G16H 20/17* (2018.01); *A61M 5/007* (2013.01); *G06F 3/1423* (2013.01); *G06V 20/46* (2022.01);
(Continued)

(58) Field of Classification Search
CPC ........ G16H 20/17; G16H 10/60; G16H 30/20; G16H 30/40; G16H 40/20; G16H 40/40;
(Continued)

(56) References Cited

U.S. PATENT DOCUMENTS

2001/0037366 A1* 11/2001 Webb ................... G16H 40/40
600/509
2002/0112733 A1* 8/2002 Miyauchi ............... G16H 40/67
600/408

(Continued)

OTHER PUBLICATIONS

Andrew Benko et al., "Canadian Association of Radiologists: Consensus Guidelines for the Prevention of Contrast-Induced Nephropathy", CARJvol. 58,No. 2,Apr. 2007 (Year: 2007).*

*Primary Examiner* — Joshua B Blanchette (57) ABSTRACT

An apparatus for use with a medical imaging device (2) operative in conjunction with a contrast injector (11) to perform a contrast enhanced medical imaging procedure. The apparatus includes: an alert output device (32), and at least one electronic processor (10, 20) operatively connected with the alert output device and programmed to: extract image frames from video or screen sharing (17) of a display (13, 24'); screen-scrape injector settings of the contrast injector from the image frames; and output an alert (30) via the alert output device if the screen-scraped injector settings satisfy an alert criterion.

19 Claims, 3 Drawing Sheets

(51) Int. Cl.
| | |
|---|---|
| *G06F 3/14* | (2006.01) |
| *G06V 20/40* | (2022.01) |
| *G06V 20/62* | (2022.01) |
| *G16H 10/60* | (2018.01) |
| *G16H 30/20* | (2018.01) |
| *G16H 30/40* | (2018.01) |
| *G16H 40/20* | (2018.01) |
| *G16H 40/40* | (2018.01) |
| *G16H 40/67* | (2018.01) |
| *G16H 70/20* | (2018.01) |
| *A61B 5/055* | (2006.01) |
| *A61B 6/03* | (2006.01) |
| *G06V 30/10* | (2022.01) |

(52) U.S. Cl.
CPC ............. *G06V 20/62* (2022.01); *G16H 10/60* (2018.01); *G16H 30/20* (2018.01); *G16H 30/40* (2018.01); *G16H 40/20* (2018.01); *G16H 40/40* (2018.01); *G16H 40/67* (2018.01); *G16H 70/20* (2018.01); *A61B 5/055* (2013.01); *A61B 6/032* (2013.01); *A61B 6/037* (2013.01); *A61M 2205/18* (2013.01); *A61M 2205/3306* (2013.01); *A61M 2205/3553* (2013.01); *A61M 2205/502* (2013.01); *G06V 30/10* (2022.01)

(58) Field of Classification Search
CPC ....... G16H 40/67; G16H 70/20; A61M 5/007; A61M 2205/18; A61M 2205/3306; A61M 2205/3553; A61M 2205/502; G06F 3/1423; G06V 20/46; G06V 20/62; G06V 30/10; G06V 2201/03; A61B 5/055; A61B 6/032; A61B 6/037; A61B 6/481; G09G 2358/00; G09G 2370/02; G09G 2380/08

See application file for complete search history.

(56) References Cited

U.S. PATENT DOCUMENTS

| | | | |
|---|---|---|---|
| 2007/0239377 A1* | 10/2007 | Reiner | G16H 30/20 250/252.1 |
| 2008/0312963 A1* | 12/2008 | Reiner | G06Q 10/06398 705/7.42 |
| 2009/0094058 A1* | 4/2009 | Reiner | G16H 20/10 705/3 |
| 2011/0238082 A1* | 9/2011 | Wenderow | A61M 25/0105 606/130 |
| 2016/0062956 A1 | 3/2016 | Gotman | |
| 2016/0092721 A1* | 3/2016 | Kanagasingam | G06V 40/193 348/78 |
| 2016/0374710 A1* | 12/2016 | Sinelnikov | A61B 17/3207 600/439 |
| 2016/0378275 A1 | 12/2016 | Akiner | |
| 2019/0129824 A1 | 5/2019 | Radhakrishnan | |
| 2020/0250826 A1* | 8/2020 | Cohen Maimon | G16H 30/20 |
| 2020/0405399 A1* | 12/2020 | Steinberg | G06N 20/00 |
| 2021/0145280 A1* | 5/2021 | Starobinets | G06F 3/04847 |

* cited by examiner

AUTOMATED SYSTEM FOR ERROR CHECKING INJECTION PARAMETERS DURING IMAGING EXAMS

CROSS REFERENCE TO RELATED APPLICATIONS

This application claims the benefit of U.S. Provisional Patent Application No. 62/938,443 filed Nov. 21, 2019. This application is hereby incorporated by reference herein.

FIELD

The following relates generally to the imaging arts, remote imaging assistance arts, remote imaging examination monitoring arts, contrast injection arts, and related arts.

BACKGROUND

Medical imaging, such as computed tomography (CT) imaging, magnetic resonance imaging (MRI), positron emission tomography (PET) imaging, fluoroscopy imaging, and so forth, is a critical component of providing medical care, and is used in a wide range of medical fields, such as cardiology, oncology, neurology, orthopedics, to name a few. The operator of the medical imaging device used to acquire the medical images is typically a trained technician, while interpretation of the medical images is often handled by a medical specialist such as a radiologist. Interpretation of radiology reports or findings by the radiologist can be handled by the patient's general practitioner (GP) physician or a medical specialist such as a cardiologist, oncologist, orthopedic surgeon, or so forth.

Nearly half of imaging exams performed on MR or CT scanners involve contrast injections, in which a contrast agent (sometime referred to as a contrast medium or other nomenclature) is intravenously administered to the patient. Depending on the type of scan, the employed contrast agent, and the anatomy in question, different injection settings and timed delays are recommended. In a mixed imaging examination that includes both non-contrast enhanced scans and contrast enhanced scans, the contrast enhanced imaging scans are usually performed last so that the contrast agent does not interfere with the non-contrast enhanced imaging.

A majority of non-contrast enhanced scans, if done incorrectly, can be rerun to achieve the desired field of view or image quality. Unfortunately, contrast enhanced imaging is an exception. In most instances, once a contrast agent is injected, the scan cannot be repeated, or at least cannot be repeated in the same imaging examination. This is due to the need for the contrast agent to fully wash out of the imaging region before the contrast enhanced imaging scan can be repeated, and in some instances also due to potential toxicity of the contrast agent. Therefore, accurately setting injection parameters on contrast injectors is essential for patient safety (for example, injecting contrast too quickly may contribute to extravasation) and for exam quality (for example, incorrect contrast injector settings can degrade clinical value of the images, and contrast scans may have a significant impact on diagnostic interpretation of the exams and/or contribute to meaningful follow-up). As the demand for imaging studies continues to grow and time pressures mount, less experienced technologists handling complex exams may struggle with correctly setting up injection protocols quickly.

The following discloses certain improvements to overcome these problems and others.

SUMMARY

In one aspect, an apparatus for use with a medical imaging device operative in conjunction with a contrast injector to perform a contrast enhanced medical imaging procedure. The apparatus includes: an alert output device, and at least one electronic processor operatively connected with the alert output device and programmed to: extract image frames from video or screen sharing of a display; screen-scrape injector settings of the contrast injector from the image frames; and output an alert via the alert output device if the screen-scraped injector settings satisfy an alert criterion.

In another aspect, a non-transitory computer readable medium stores instructions executable by at least one electronic processor to perform a method of providing assistance during a contrast enhanced medical imaging procedure. The method includes: receiving a video feed capturing the controller display disposed in a medical device imaging bay; displaying the video feed at a remote workstation display disposed in a remote location; extract image frames from the displayed video feed; screen-scraping injector settings of the contrast injector from the image frames; and outputting an alert via an alert output device if the screen-scraped injector settings satisfy an alert criterion.

In another aspect, a method for providing remote assistance to a local operator of a medical imaging device including a contrast injector disposed in a medical imaging device bay via a communication link from a remote location that is remote from the medical imaging device bay to the medical imaging device bay. The method includes: extracting image frames from video or screen sharing of a display of the medical device controller; screen-scraping injector settings of the contrast injector from the image frames; retrieving information on a contrast injection procedure from one or more databases based at least in part on the screen-scraped information; and displaying the screen-scraped injector settings and the retrieved at a workstation display.

One advantage resides in providing an independent assessment of accuracy and/or appropriateness of contrast injector settings, and providing a timely alert if the contrast injector settings appear to be inaccurate or inappropriate (e.g. outside of an acceptable setting range).

Another advantage resides in providing such verification which takes into account diverse factors such as imaging departmental standard operating procedures, the specific imaging examination, and patient-specific considerations.

Another advantage resides in providing the aforementioned independent assessment of accuracy and/or appropriateness in a manner that is vendor-agnostic as to the vendor, make, or model of the contrast injector.

Another advantage resides in providing a remote reviewer, such as a remote operator providing imaging examination support from a remote service center, or a remotely located radiologist providing image quality review during the imaging examination, with awareness of the contrast injector settings which facilitates providing assistance to a one or more local operators at different facilities, and may enable the remote reviewer to provide preemptive corrective advice to the local imaging technician.

Another advantage resides in preventing errors in contrast injector settings before the contrast agent is injected into the patient.

Another advantage resides in avoiding delaying of imaging procedures based on incorrect contrast injector settings.

Another advantage resides in avoiding multiple contrast agent dose administered to a patient.

Another advantage resides in providing a remote operator or radiologist with contrast injector settings on a medical imaging examination using a standard display format that is independent of the display of the contrast injector used in the medical imaging examination.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

A critical aspect of many imaging examinations can be the contrast injection process. In a typical workflow, the patient has the intravenous (IV) needle already inserted, and this is connected to the feedline of the contrast injector at the time the patient is loaded into the imaging system. Imaging sequences that employ a contrast agent are usually performed last, so that residual contrast agent in the patient do not impact non-contrast-enhanced imaging. Hence, a local technician may program the contrast injector settings as the earlier imaging sequences are underway. When the time comes for the final contrast enhanced imaging sequence, the patient is advised that the contrast agent is about to be administered. The contrast injector is usually programmed with a delay setting—the technician arms and activates the injector and at about the same time starts the contrast enhanced imaging sequence. In this way, initial reference non-contrast-enhanced images are acquired during the delay, and the imaging sequence continuously acquires a cinematic (CINE) sequence of images to capture inflow and washout of the contrast agent.

Any error in the contrast injector settings is usually irrecoverable, since the contrast agent may take a long time to fully wash out of the imaging region before another contrast injection can be performed, and moreover toxicity concerns may prevent a second contrast agent injection in the same day. The appropriate contrast injector settings can depend on a number of factors, such as the specific imaging examination being performed, characteristics of the patient (for example, the contrast agent may be designed to be administered at a specific dose per unit mass of the patient, so that the dose depends on patient weight; in another example, the patient may have a medical condition for which a particular contrast agent is contraindicated), standard operating procedures (SOP) of the imaging department, and so forth. Given this diversity of factors, along with the busy multitasking environment of the imaging laboratory, it is possible for the imaging technician to make an error in setting up the contrast injector.

In some embodiments disclosed herein, a system and method are disclosed for performing independent assessment of the accuracy and/or appropriateness of the contrast injector settings, and for providing an alert of any detected potentially erroneous injector settings prior to commencement of the contrast-enhanced (portion of the) imaging examination. To this end, screen scraping of the injector display can be leveraged to automatically extract the programmed contrast injector settings. The injector display content may be scraped from a shared screen (for example, in the context of a remote-assisted examination in which the injector display is shared with the super-tech's computer) or from frames of a video camera whose field of view includes the injector display. Using the shared screen as the source for the screen scraping can be more accurate compared with screen scraping of video, as a video camera view may be occasionally occluded by movement of personnel and may have low resolution; however, not all equipment displays will necessarily be screen-shared with the technician, in which case a camera-based screen scraping is suitable.

In other embodiments disclosed herein, a machine-interpretable copy of the standard operating procedure (SOP) guidelines of the imaging laboratory is provided. The screen-scraped injector settings are compared against the SOP guidelines, and any SOP non-compliance results in an alert being issued.

In some embodiments disclosed herein, screen scraping of the console display is performed to determine the CA-enhanced scanning protocol being employed. The system also accesses patient screening form(s), the Electronic Medical Record (EMR) or other patient database to obtain patient information that may affect the appropriate injector settings, such as patient weight and age (e.g. is the patient a pediatric patient?). The screen-scraped injector settings are then compared against appropriate contrast injector settings or setting ranges computed for the scanning protocol and patient information. An alert is issued if the screen-scraped injector settings deviate significantly from these appropriate values.

In other embodiments disclosed herein, the screen-scraped injector settings along with the associated scanning protocol and patient information are stored in a database, and can be used for subsequent quality assurance assessments or the like.

In the event that the system detects a possibly erroneous contrast injector setting, an alert is provided. This alert may be provided to the (local) imaging technician who is performing the imaging examination. Additionally or alternatively, the alert may be provided to a remote reviewer who is in communication with the local imaging technician. For example, the disclosed system and method may be usefully integrated with a remote radiology operations command center service, in which a remotely based senior technician (i.e. "super-tech") is provided with a camera view of a scanner and console rooms along with screen sharing of the console display, and can provide telephonic or other assistance to the local technician during challenging imaging examinations.

Ideally, the super-tech will monitor critical aspects of the imaging examination, such as the contrast injector settings, and provide advice/correction if the local technician incorrectly sets up the contrast injector. However, there is a significant possibility that the super-tech may fail to notice incorrect contrast injector setup. The super-tech can be expected to be simultaneously handling a number of different imaging bays, and hence cannot be continuously monitoring any one imaging examination. Moreover, the super-tech's interaction with the local technician may draw attention away from the contrast injector settings. As previously noted, the local technician may set up the contrast injector while earlier non-contrast enhance imaging scans are performed. During such times, the super-tech will likely be attentive to the ongoing non-contrast enhanced imaging, and may not pay sufficient attention to the injector setup. The disclosed system and method can advantageously provide the alert of a possibly erroneous contrast injector setting to the super-tech (instead of, or in addition to, providing the alert to the local technician), thereby drawing the super-tech's attention to the contrast injector settings.

In similar fashion, the alert indicating a possibly erroneous contrast injector setting may be issued to other remote reviewers, such as to an on-call radiologist. In some imaging examinations, an on-call radiologist may be consulted during the imaging examination in order to review/approve acquired clinical images while the patient is still loaded in the imaging device. In this way, any clinical images of insufficient quality can be re-acquired. In some setups the on-call radiologist may review the clinical images remotely, e.g. by having the images transmitted to a radiology workstation used by the radiologist that is remote from the imaging laboratory. In such a setup, the disclosed system and method can advantageously provide the alert of a possibly erroneous contrast injector setting to the on-call radiologist (instead of, or in addition to, providing the alert to the local technician), and the radiologist can then review the contrast settings and provide corrective advice to the local technician if needed.

Figure 1:
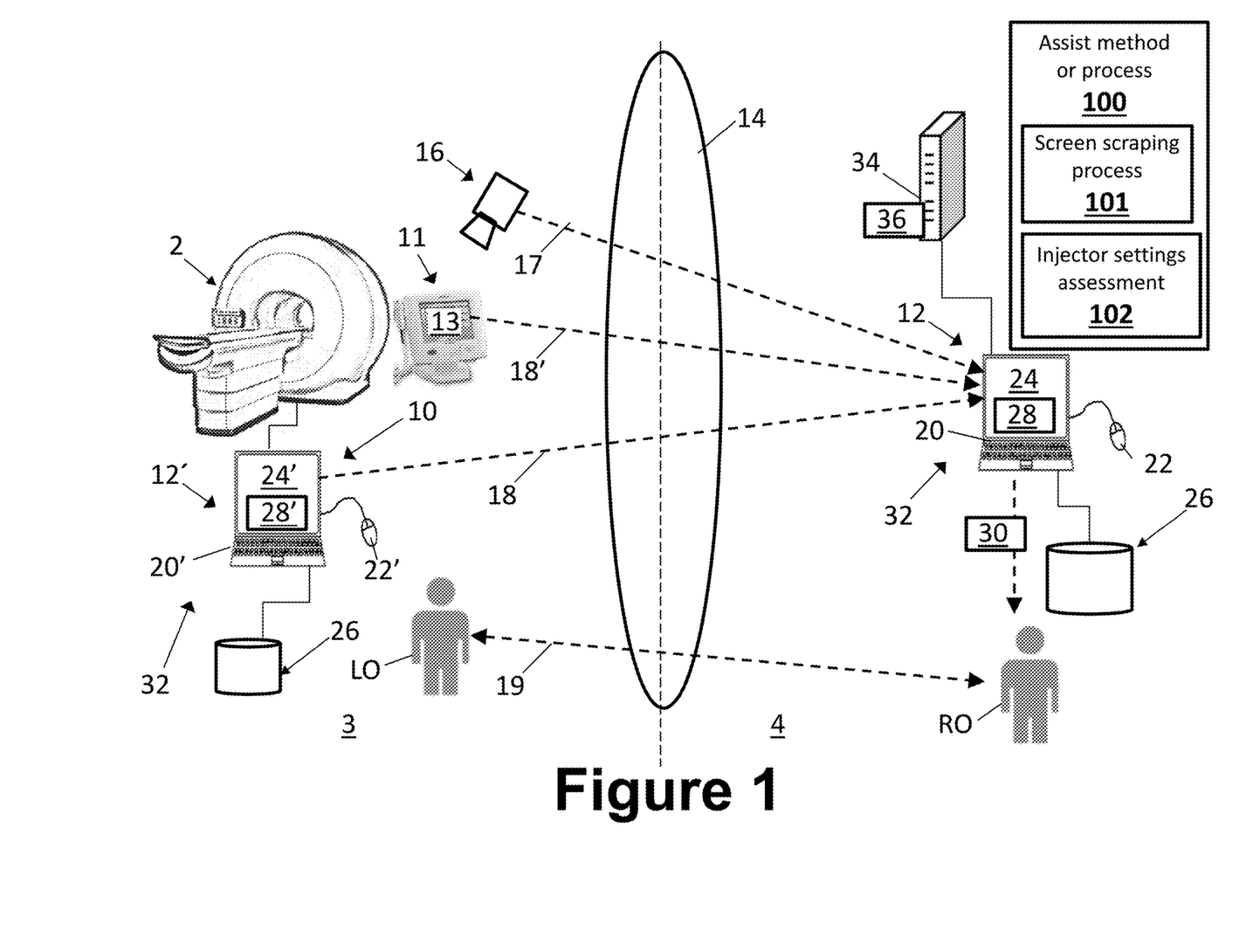
FIG. 1 diagrammatically shows an illustrative apparatus for providing remote assistance in accordance with the present disclosure.

With reference to FIG. 1, the system and method for independently assessing contrast injector settings, and alerting if inaccurate or inappropriate settings are detected, is described in the illustrative context of an apparatus for providing assistance from a remote operator RO (or super-tech) to a local operator LO is shown. As shown in FIG. 1, the local operator LO, who operates a medical imaging device (also referred to as an image acquisition device, imaging device, and so forth) 2, is located in a medical imaging device bay 3, and the remote operator RO is disposed in a remote service location or center 4. It should be noted that the "remote operator" RO may not necessarily directly operate the medical imaging device 2, but rather provides assistance to the local operator LO in the form of advice, guidance, instructions, or the like. The remote location 4 can be a remote service center, a radiologist's office, a radiology department, and so forth. The remote location 4 may be in the same building as the medical imaging device bay 3 (this may commonly be the case, for example, in the case of a "remote operator" RO who is a radiologist tasked with peri-examination image review), but more typically the remote service center 4 and the medical imaging device bay 3 are in different buildings, and indeed may be located in different cities, different countries, and/or different continents. In general, the remote location 4 is remote from the imaging device bay 3 in the sense that the remote operator RO cannot directly visually observe the imaging device 2 in the imaging device bay 3 (hence optionally providing a video feed as described further herein).

The image acquisition device 2 can be a Magnetic Resonance (MR) image acquisition device, a Computed Tomography (CT) image acquisition device; a positron emission tomography (PET) image acquisition device; a single photon emission computed tomography (SPECT) image acquisition device; an X-ray image acquisition device; an ultrasound (US) image acquisition device; or a medical imaging device of another modality. The imaging device 2 may also be a hybrid imaging device such as a PET/CT or SPECT/CT imaging system. While a single image acquisition device 2 is shown by way of illustration in FIG. 1, more typically a medical imaging laboratory will have multiple image acquisition devices, which may be of the same and/or different imaging modalities. For example, if a hospital performs many CT imaging examinations and relatively fewer MRI examinations and still fewer PET examinations, then the hospital's imaging laboratory (sometimes called the "radiology lab" or some other similar nomenclature) may have three CT scanners, two MRI scanners, and only a single PET scanner. This is merely an example. Moreover, the remote service center 4 may provide service to multiple hospitals. The local operator controls the medical imaging device 2 via an imaging device controller 10. The remote operator is stationed at a remote workstation 12 (or, more generally, an electronic controller 12).

To provide for contrast enhanced imaging, a contrast injector 11 is configured to inject the patient with a contrast agent. The contrast injector 11 is a configurable automated contrast injector having a display 13. The user (usually the imaging technician) loads a vial or syringe of contrast agent (or two, or more, vials of different contrast agent components) into the contrast injector 11, and configures the contrast injector 11 by entering contrast injector settings such as flow rates, volumes, time delays, injection time durations, and/or so forth via a user interface (UI) of the contrast injector 11. The UI may be a touch-sensitive overlay of the display 13, and/or physical buttons, keypad, and/or so forth. In a variant embodiment, the contrast injector 11 is integrated with the imaging device controller 10 (e.g., via a wired or wireless data connection), and the contrast injector 11 is controlled via the imaging device controller 10, including displaying the contrast injector settings in a (optionally selectable) window on the display of the imaging device controller 10. In such an embodiment, the dedicated physical injector display 13 of the contrast injector may optionally be omitted (or, alternatively, the dedicated physical injector display 13 may be retained and the contrast settings displayed at both the dedicated physical injector display 13 and at the imaging device controller 10). In general, the automated contrast injector 11 can employ any suitable mechanical configuration for delivery of the contrast agent (or agents), such as being a syringe injector, a dual-syringe injector, pump-driven injector, or so forth, and may include hardware for performing advanced functions such as saline dilution of the contrast agent, priming and/or flushing of the contrast injection line with saline, and/or so forth.

As used herein, the term "medical imaging device bay" (and variants thereof) refer to a room containing the medical imaging device 2 and also any adjacent control room containing the medical imaging device controller 10 for controlling the medical imaging device. For example, in reference to an MRI device, the medical imaging device bay 3 can include the radiofrequency (RF) shielded room containing the MRI device 2, as well as an adjacent control room housing the medical imaging device controller 10, as understood in the art of MRI devices and procedures. On the other hand, for other imaging modalities such as CT, the imaging device controller 10 may be located in the same room as the imaging device 2, so that there is no adjacent control room and the medical bay 3 is only the room containing the medical imaging device 2. In addition, while FIG. 1 shows a single medical imaging device bay 3, it will be appreciated that the remote service center 4 (and more particularly the remote workstation 12) is in communication with multiple medical bays via a communication link 14, which typically comprises the Internet augmented by local area networks at the remote operator RO and local operator LO ends for electronic data communications. In other embodiments, there may be no remote center 4, a remote workstation 12, and/or a remote operator RO. In this embodiment, only the local operator LO is monitoring the medical imaging device controller 10.

As diagrammatically shown in FIG. 1, a camera 16 (e.g., a video camera) is arranged to acquire a video stream 17 of a portion of the medical imaging device bay 3 that includes at least the area of the imaging device 2 where the local operator LO interacts with the patient, and optionally may further include the imaging device controller 10 and/or the contrast injector 11. The video stream 17 is sent to the remote workstation 12 via the communication link 14, e.g. as a streaming video feed received via a secure Internet link. In embodiments in which the contrast injector 17 includes the dedicated physical injector display 13, the field of view (FOV) of the camera 16 may encompass the dedicated physical injector display 13, so that the content of the display 13 is captured in the video stream 17, Additionally, a screen mirroring data stream 18 is sent from the imaging device controller 10 to the remote workstation 12. The communication link 14 also provides a natural language communication pathway 19 for verbal and/or textual communication between the local operator and the remote operator. For example, the natural language communication link 19 may be a Voice-Over-Internet-Protocol (VOIP) telephonic connection, an online video chat link, a computerized instant messaging service, or so forth. Alternatively, the natural language communication pathway 19 may be provided by a dedicated communication link that is separate from the communication link 14 providing the data communications 17, 18, e.g. the natural language communication pathway 19 may be provided via a landline telephone.

FIG. 1 also shows, in the remote service center 4 including the remote workstation 12, such as an electronic processing device, a workstation computer, or more generally a computer, which is operatively connected to receive and present the video 17 of the medical imaging device bay 3 from the camera 16 and to present the screen mirroring data stream 18 as a mirrored screen. Additionally or alternatively, the remote workstation 12 can be embodied as a server computer or a plurality of server computers, e.g. interconnected to form a server cluster, cloud computing resource, or so forth. The workstation 12 includes typical components, such as an electronic processor 20 (e.g., a microprocessor), at least one user input device (e.g., a mouse, a keyboard, a trackball, and/or the like) 22, and at least one display device 24 (e.g. an LCD display, plasma display, cathode ray tube display, and/or so forth). In some embodiments, the display device 24 can be a separate component from the workstation 12. The display device 24 may also comprise two or more display devices, e.g. one display presenting the video 17 and the other display presenting the shared screen of the imaging device controller 10 generated from the screen mirroring data stream 18. Alternatively, the video and the shared screen may be presented on a single display in respective windows. The electronic processor 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the workstation 12, various combinations thereof, or so forth. It is to be understood that any reference to a non-transitory medium or media 26 herein is to be broadly construed as encompassing a single medium or multiple media of the same or different types. Likewise, the electronic processor 20 may be embodied as a single electronic processor or as two or more electronic processors. The non-transitory storage media 26 stores instructions executable by the at least one electronic processor 20. The instructions include instructions to generate a graphical user interface (GUI) 28 for display on the remote operator display device 24.

The medical imaging device controller 10 in the medical imaging device bay 3 also includes similar components as the remote workstation 12 disposed in the remote service center 4. Except as otherwise indicated herein, features of the medical imaging device controller 10, which includes a local workstation 12', disposed in the medical imaging device bay 3 similar to those of the remote workstation 12 disposed in the remote service center 4 have a common reference number followed by a "prime" symbol, and the description of the components of the medical imaging device controller 10 will not be repeated. In particular, the medical imaging device controller 10 is configured to display a GUI 28' on a display device or controller display 24' that presents information pertaining to the control of the medical imaging device 2, such as configuration displays for adjusting configuration settings an alert 30 perceptible at the remote location when the status information on the medical imaging examination satisfies an alert criterion of the imaging device 2, imaging acquisition monitoring information, presentation of acquired medical images, and so forth. In embodiments discussed previously in which the contrast injector 11 is controlled via the medical imaging device controller 10, the contrast injector settings are displayed on the display 24' of the medical imaging device controller 10 (and, in such embodiments, the dedicated physical injector display 13 is optionally omitted). It will be appreciated that the screen mirroring data stream 18 carries the content presented on the display device 24' of the medical imaging device controller 10. In embodiments in which the contrast injector 11 is controlled via the medical imaging device controller 10, the mirrored content carried by the screen mirroring data stream 18 thus includes the display of the contrast injector settings. In embodiments in which the contrast injector 11 includes the dedicated physical injector display 13, the display 13 may be separately mirrored at the display device 24 in the remote service center 4, for example being displayed in a separate window on the display device 24. In these embodiments, a second screen mirroring data stream 18' carries the content presented on the dedicated physical injector display 13. The communication link 14 allows for screen sharing between the display device 24 in the remote service center 4 and the display device 24' in the medical imaging device bay 3. The GUI 28' includes one or more dialog screens, including, for example, an examination/scan selection dialog screen, a scan settings dialog screen, an acquisition monitoring dialog screen, among others. The GUI 28' can be included in the video feed 17 or the mirroring data stream 17' and displayed on the remote workstation display 24 at the remote location 4.

The remote workstation 12 is configured as described above to perform a method or process 100 for providing assistance the local operator LO, including at least independently assessing contrast injector settings, and alerting if inaccurate or inappropriate settings are detected. By "independently" it is meant that the assessment 100 is performed independently of the local operator LO, and is performed independently of any setting limits coded into the contrast injector 11. The method or process 100 includes a screen sharing process 101 which performs screen scraping on the controller display 24' of the medical imaging device 2, and the method or process 100 includes maintaining status information on the ongoing medical imaging examination, optionally in particular including status information on the injection of the contrast agent into the patient, based on information obtained by the screen scraping 101. The screen scraping process 101 operates to extract (from the video 17 or the screen sharing 18) image frames of the controller display 24' of the medical imaging device 2, and to screen-scrape information related to the status of the imaging procedure from the successive image frames over the course of the medical imaging examination. Furthermore, an injector settings assessment 102 is performed, which in particular extracts the injector settings of the contrast injector 11 via the screen scraping process 101 and assesses whether the injector settings are accurate or appropriate based on various pieces of information, and if an inaccurate or inappropriate contrast injector setting is identified then an alert is issued.

The non-transitory storage medium 26 stores instructions which are readable and executable by the at least one electronic processor 20 (of the workstation 12, as shown, and/or the electronic processor or processors of a server or servers on a local area network or the Internet) to perform disclosed operations including performing the method or process 100 (including the screen scraping process 101 and the injector settings assessment 102). In some examples, the method 100 may be performed at least in part by cloud processing. In particular, the GUI 28 presented on the display 24 of the remote workstation 12 preferably includes a window presenting the video 17, and a window presenting the mirrored screen of the medical imaging device controller 10 constructed from the screen mirroring data stream 18, and status information on the medical imaging examination that is maintained at least in part using the screen-scraped information. This allows the remote operator RO to be aware of the content of the display of the medical imaging device controller 10 (via the shared screen) and also to be aware of the physical situation, e.g. position of the patient in the medical imaging device 2 (via the video 17), and optionally to additionally be aware of the status of the contrast injection process of the imaging examination as summarized by the status information. During an imaging procedure, the natural language communication pathway 19 is suitably used to allow the local operator LO and the remote operator RO to discuss the contrast injection settings and in particular to allow the remote operator to provide advice to the local operator.

The method 100 includes outputting an alert 30 if the injector settings in the screen-scraped image frames (from the video 17 or the screen sharing 18) satisfy an alert criterion. To do so, an alert output device (indicated generally with 32) outputs the alert 30. In some examples, the alert output device can be the display device 24 of the remote workstation 12, the controller device 24' of the medical imaging device 2, or the contrast injector display 13 of the contrast injector 11. The alert output device can also be a loudspeaker (not shown) of the remote workstation 12 of the imaging device controller 10. In other examples, the alert output device can be a personal device of the remote operator RO and/or the local operator LO, such as a smart phone, tablet, personal digital assistant, and so forth. In this case, the alert 30 can be output as a text message or an audio message on the personal device.

Figure 2:
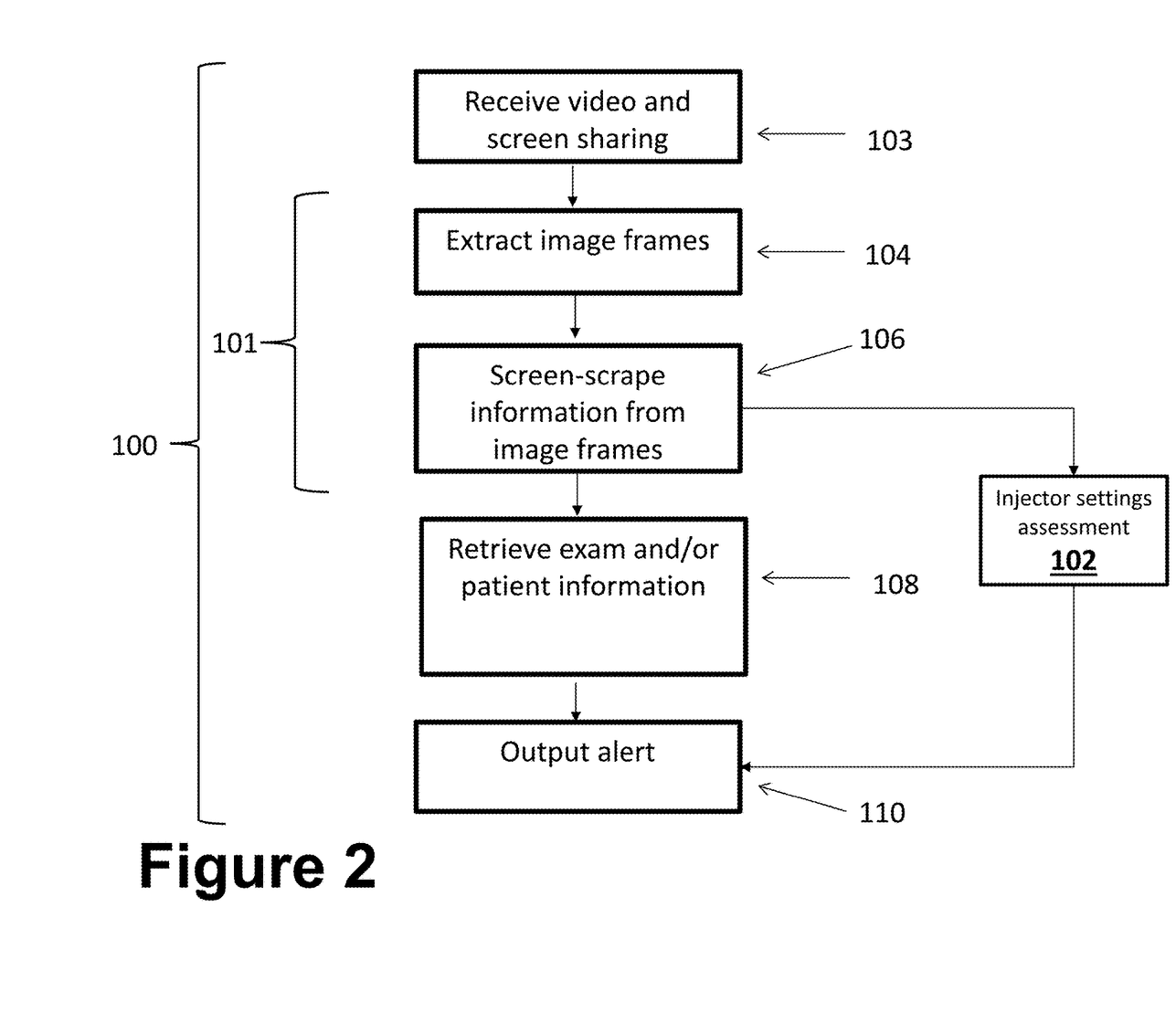
FIG. 2 shows an example flow chart of operations suitably performed by the apparatus of FIG. 1.

With reference to FIG. 2, and with continuing reference to FIG. 1, an illustrative embodiment of the method 100 is diagrammatically shown as a flowchart. The method 100 is performed over the course of a medical imaging examination performed using the medical imaging device 2. At an operation 103, the at least one electronic processor 20 of the workstation 12 in the remote location 4 is programmed to receive at least one of: video 17 from the video camera 16 of the medical imaging device 2 and/or the contrast injector 11 located in the medical imaging device bay 3; and/or the screen sharing 18. The video feed 17 and/or the screen sharing 18 can be displayed at the remote workstation display 24, typically in separate windows of the GUI 28.

At an operation 104, the at least one electronic processor 20 of the workstation 12 in the remote location 4 is programmed to extract image frames from the video 17 or from the screen sharing 18 of the controller display 24' of the medical imaging device 2 and/or contrast injector display 13 of the contrast injector 11. The extracted image frames are typically successive image frames, but may not necessarily include every image frame of the acquired video or screen sharing. For example, the video or screen sharing might be at 30 frames per sec (fps), but the screen scraping might only be able to process 5 fps due to computational limitations. In that case, the successive image frames might be every sixth video frame. The screen-scraped frames may also be non-periodic, e.g. if computational speed of frame processing varies from frame to frame due to content complexity, then the number of intervening video frames between successive screen-scraped frames may vary. The extracted successive frames are bitmap images. These bitmap images may be color or monochrome images, depending on the source video 17 or screen sharing 18 and, in the case of color video or screen sharing, depending on whether the extraction operation 104 retains the color information. The extracted successive frames contain information such as details of the imaging protocol being acquired, aborted or repeated image sequences, an amount of time left in the medical exam, error messages generated by the imaging device 2, patient breathing, heart rate waveforms, a patient screening form, and so forth. However, the information is contained in bitmap image form, and hence is not readily machine interpretable.

Accordingly, at an operation 106, the at least one electronic processor 20 of the workstation 12 in the remote location 4 is programmed to screen-scrape status information related to the medical imaging examination, such as the injector settings of the contrast injector 11, from the extracted successive image frames before the medical imaging examination (although this operation may take place in the medical device imaging bay 3 and transmitted to the remote location). The extraction and screen scraping operations 104, 106 correspond to the screen-scrapping process 101 of FIG. 1. In one example, the screen-scraping operation 106 includes performing OCR processes on an image frame under analysis by the remote operator RO to extract textual information related to the status information (e.g., injector settings). In another example, the screen-scraping operation 106 includes annotating the screen-scraped information with an identification of the contrast enhanced medical imaging procedure in the non-transitory computer readable medium 26. Although described below in terms of a single imaging device bay 3, the at least one electronic processor 20 can be iteratively executing a plurality of instances of the operations 104, 106 to screen-scrape video 17 (or screen-sharing 18) of a corresponding plurality of medical imaging devices 2 and/or contrast injectors 11 disposed at a corresponding number of medical imaging devices bays 3.

At an operation 108, the at least one electronic processor 20 is programmed to retrieve information from one or more databases 34 (e.g., a Picture Archiving and Communication System (PACS) database, a health information system (HIS) database, a radiology information system (RIS) database, an Electronic Medical Record (EMR) database, and Electronic Health Record (EHR) database, and so forth), based on the screen-scraped status information (e.g., injector settings). At an operation 110, the at least one electronic processor 20 is programmed to control the alert output device 32 to output the alert 30 if the screen-scraped settings (and, optionally, the retrieved information) satisfy an alert criterion.

As further shown in FIG. 2, the screen scraping 106 (or an analogous separate screen scraping operation, for example operating on the content of the dedicated physical injector display 13) is also used to perform the injector settings assessment 102. If the injector settings assessment 102 detects an injector setting that is inaccurate or inappropriate based on information gathered by the injector settings assessment 102, then the alert operation 110 (or an analogous alert operation specifically designed for the injector settings assessment 102) can suitably be issued.

Figure 3:
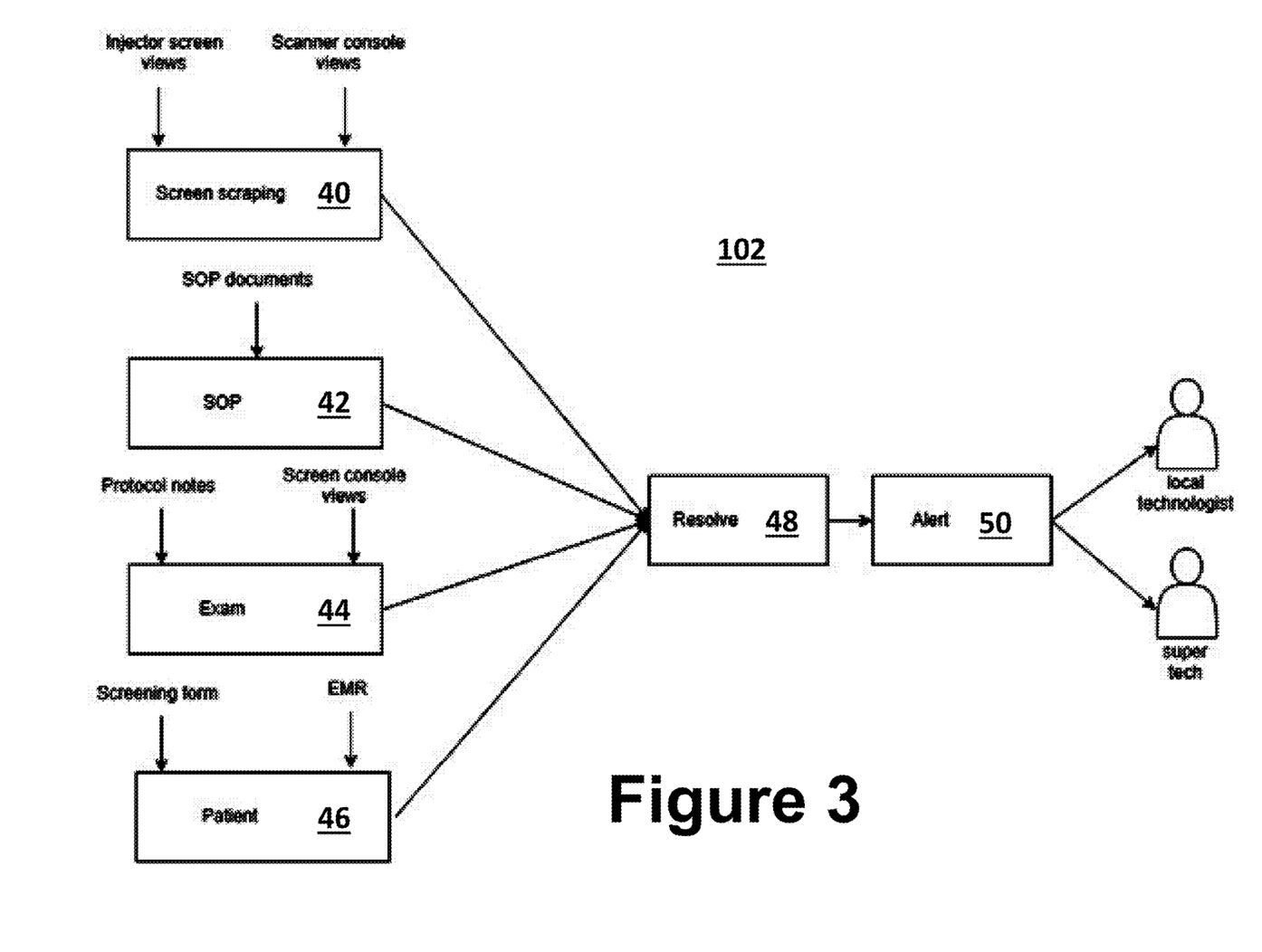
FIG. 3 shows another example flow chart of operations suitably performed by the apparatus of FIG. 1.

With reference now to FIG. 3, an illustrative embodiment of the injector settings assessment 102 is described. The injector settings assessment 102 can be performed in a variety of manners, not necessarily being mutually exclusive. In one example, the at least one electronic processor 20 is programmed to retrieve information related to the patient to be injected with the contrast agent from the PACS or EMR or EHR database 34 (e.g., weight, age, gender, allergies, presence of medical implants, presence of allergies, and so forth). Based on this retrieved information, the alert 30 is output when the screen-scraped injector settings satisfy an alert criterion. For example, in a typical contrast agent injection procedure, the contrast agent can have a maximum dose of approximately 0.1 mL//kg of body weight (which can be retrieved from one of more of the guideline documents 36). If the weight of the patient retrieved from the database 34 indicates that the weight of the patient is 200 kg, then the contrast agent dose amount should be 20 mL (0.1 mL/kg*200 kg). If the screen-scraped information indicates that the dose amount is higher or lower than 20 mL, then the alert 30 is output. In another example, contrast agent injection procedures can include dose levels for pediatric patients and adults. Once the patient's age is retrieved, the alert 30 can be output if, for example, the adult dose level is being used for a child (or vice versa). Similar alerts 30 can be output for flow rate, presence of allergies to the contrast agent, presence of medical implants, and so forth.

In another example, the at least one electronic processor 20 is programmed to retrieve one or more guideline documents 36 related to the imaging and/or the injection procedure from the HIS or RIS database 34. The guideline documents 36 can include information related to temporal information related to the contrast enhanced medical imaging procedure, a maximum contrast flow rate value, and so forth. The alert 30 can be output based on, for example, a comparison between the screen-scraped timed injection delay and the time delay information in the guideline documents 36, a comparison between the screen-scraped flow rate the maximum flow rate in the guideline documents, and so forth.

As shown in FIG. 3, a screen-scraping operation 40 performs the screen-scraping of a display that shows the injector settings of the contrast injector 11. The operation 40 may be performed in various ways, depending upon the user interface being employed with the contrast injector 11. For example, if the imaging device controller 10 also controls the contrast injector 11 and displays the injector settings, then the screen-scraping operation 40 is suitably implemented as the screen scraping operation 106 of FIG. 2 which is configured to screen scrape the controller display 24', either by processing the video feed 17 if it captures the controller display 24', or by processing the screen sharing data 18. Alternatively, if the dedicated physical injector display 13 is employed, then the screen-scraping operation 40 suitably operates on the video feed 17 (but processing the portion of the video frames capturing the display 13) or operates on the screen sharing data 18' of the dedicated physical injector display 13. (In another contemplated embodiment, a separate video camera, not shown, may be specifically positioned to capture the dedicated physical injector display 13, and that video feed would then be screen-scraped.

The screen-scraping operation 40 extracts specific injector settings by performing OCR on the captured image of the display (or the portion of the display containing the injector settings). Specific injector settings can be extracted from the OCR-generated text in various ways. In one approach, if an injector settings display template is available, then the template can directly identify the informational content since the injector settings display template will identify which regions of the display contain which settings. However, this approach depends on the injector settings display template being correct for the specific vendor/model of the contrast injector 11 (or of the imaging device controller 10 if the latter is used to control the contrast injector 11). A database of templates may be stored for different vendor/models, and the correct template is contemplated to be identified based on comparison of the screen image with the various templates, and/or based on the OCR-generated text (e.g., the vendor name may be shown on the display and extracted by the OCR, thereby allowing the vendor to be identified). In another approach, the OCR-generated text (and associated location anchoring in the image of the display) may provide textual context for associating a value with a particular injector setting. For example, a numerical value which is spatially adjacent to the OCR-generated text "Flow rate" and OCR-generated text "mL/s" can thereby be identified as the flow rate injector setting measured in milliliters per second. These are merely illustrative examples, and additional/other approaches for screen scraping the injector settings are contemplated.

The injector settings obtained by screen scraping are then compared with various informational sources to detect any injector setting that is inaccurate or inappropriate. In the illustrative example, the informational sources include the standard operating procedure (SOP) for the imaging laboratory, information on the particular imaging examination being performed, and information on the patient. Hence, in an operation 42, SOP information is extracted from the SOP documents, for example using OCR (if the documents are not in a directly machine-readable structure format). Similar to the identification of the injector settings in the scraped screen, this can entail identifying numerical values with proximate labels (e.g. a numerical value with proximate identifiers: "maximum flow rate" and "mL/s", may be processed to identify the maximum contrast agent flow rate). Alternatively, the SOP information may be stored in a machine-readable structured format, in which case operation 42 entails retrieving that date structure containing SOP constraints on the injector settings.

In an operation 44, the imaging examination information is extracted. This may entail identifying the imaging examination being performed, for example using information obtained by the screen scraping 106 performed on the controller display 24' during the imaging examination, or by retrieving the examination order stored in the RIS, or so forth. An internal database may suitably store injector settings or injector setting value ranges for various imaging procedures, and hence the determination of the imaging examination being performed permits retrieval of the injector settings or injector setting value ranges for that (type of) imaging examination. In an operation 46, relevant patient information such as patient weight, patient classification (e.g., juvenile or adult), chronic conditions that might contraindicate use of certain contrast agents, and so forth is extracted from the PACS or EMR or EHR database.

With the injection settings obtained by the screen scraping 40, and other relevant information collected by the operations 42, 44, 46, in an operation 48 the collected information is applied to resolve whether the screen-scraped injection settings are accurate or appropriate. For example, any injector setting that lies outside of a permissible range given in the SOP is detected as an inappropriate injector setting. In some cases, information may be combined. For example, if the examination information from operation 44 indicates that the contrast agent should be delivered at 0.05 mL/s/kg, and the patient information obtained at operation 46 indicates that the patient weighs 70 kg, then it can be computed that the flow rate injector setting should be (0.05 mL/s/kg)×(70 kg)=3.5 mL/s. Since the patient weight extracted from the EMR or EHR may differ somewhat from the patient weight used by the imaging technician (which may, for example, be a weight measured as part of the pre-exam patient processing), an inaccurate flow rate injector setting is detected if the screen-scraped flow rate is outside of some range centered around the computed 3.5 mL/s, e.g. if it is outside of the range 3.0-4.0 mL/sec in one example. As another example, if the patient information obtained at operation 46 indicates the patient has a condition that contraindicates contrast agent "X", and the screen-scraped injector settings indicate that the contrast agent loaded into the contrast injector 11 is contrast agent "X", then this is detected as an inappropriate injector setting. These are merely illustrative alert criteria, and additional/fewer/different alert criteria may be applied by the resolution operation 48.

At an operation 50, if an alert criterion is met or satisfied at the resolution operation 48, then an alert 30 is output to the local operator LO and/or to the remote operator RO. Preferably, the alert 30 identifies at least the injector setting for which an error is detected and some information about why the injector setting is detected as erroneous. For the examples of the preceding paragraph, suitable alerts might be articulated as (for example): "Warning: Injector setting <X> lies outside of the permissible range of <YY-YY>specified in <SOP document identification>"; or "Warning: the flow rate of <flow rate injector setting> appears to be in error. The flow rate for imaging procedure <Proc-ID>should be 0.05 mL/s/kg. Patient <Patient-ID> weighed 70 kg as of <EMR weight date>. Based on this information, it appears the flow rate should be 3.5 mL/s"; or "Warning: The contrast injector is loaded with contrast medium "X"; however, according to <EMR doc-ID>, patient <patient-ID> has <chronic condition> for which contrast medium "X" is contraindicated." Again, these are merely examples.

In the illustrative embodiment, the injector settings assessment 102 is implemented in the context of an apparatus for providing assistance from a remote operator RO (or super-tech) to a local operator LO as shown in FIG. 1, and is implemented on the remote server 34. However, it will be appreciated that the disclosed the injector settings assessment 102 can be used independently from any remote operator assistance apparatus, and/or may be implemented elsewhere. For example, the injector settings assessment 102 could be implemented locally on the imaging device controller 10 or on a hospital information technology (IT) server communicating with the imaging device controller 10, and may provide alerts only to the (local) imaging technician.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A system for use in performing a contrast enhanced medical imaging procedure, the system comprising:
   a medical imaging device disposed in a medical imaging device bay;
   a contrast injector disposed in the medical imaging device bay;
   a camera disposed in the medical imaging device bay and positioned to have a field of view including at least the contrast injector;
   a workstation disposed in a remote service center that is remote from the medical imaging device bay, the camera being connected with the workstation; and
   an alert output device comprising one of the medical imaging device or the workstation; and
   wherein the workstation comprises at least one electronic processor operatively connected with the alert output device and programmed to:
      perform video or screen sharing in which a display of the medical imaging device or the contrast injector which presents injector settings of the contrast injector is shared at a remote workstation display;
      extract image frames from the video or screen sharing of the display of the medical imaging device or the contrast injector;
      screen-scrape the injector settings of the contrast injector from the image frames; and
      output an alert via the alert output device if the screen-scraped injector settings satisfy an alert criterion.

2. The system according to claim 1, wherein the at least one electronic processor is programmed to:
   retrieve a weight of a patient undergoing the contrast enhanced medical imaging procedure from a patient database;
   wherein the alert criterion is based on the weight of the patient.

3. The system according to claim 1, wherein the at least one electronic processor is programmed to:
   retrieve an age of a patient undergoing the contrast enhanced medical imaging procedure from a patient database;
   wherein the alert criterion is based on the age of the patient.

4. The system according to claim 1, wherein the screen scraped injector settings include a screen scraped timed injection delay and the at least one electronic processor is programmed to:
   retrieve temporal information related to the contrast enhanced medical imaging procedure from one or more guideline documents stored in a database based on the screen-scraped injection parameters;

wherein the alert criterion includes a criterion based on comparison of the screen-scraped timed injection delay and a range of temporal delay values in the retrieved documents.

5. The system according to claim 1, wherein the screen scraped injector settings include a screen scraped contrast flow rate and the at least one electronic processor is programmed to:

retrieve a maximum contrast dose amount value from one or more guideline documents stored in a database;

wherein the alert criterion is based on comparison of the screen scraped contrast dose amount and the maximum dose amount.

6. The system according to claim 1, wherein the at least one electronic processor is programmed to:

store the screen-scraped injector settings annotated by an identification of the contrast enhanced medical imaging procedure in a database.

7. The system according to claim 1, wherein the display is the display of the medical imaging device.

8. The system according to claim 7, wherein the alert output device comprises the remote workstation display.

9. The system according to claim 1, wherein the alert output device comprises the display of the medical imaging device.

10. A non-transitory computer readable medium storing instructions executable by at least one electronic processor to perform a method of providing assistance during a contrast enhanced medical imaging procedure, the method comprising:

receiving a video stream capturing the controller display disposed in a medical imaging device bay from a camera disposed in the medical imaging device bay, the controller display showing both a control user interface for the medical imaging device and the injector settings of the contrast injector;

video-sharing the video stream at a remote workstation display disposed in a remote location that is a different location than a location where the contrast enhanced medical imaging procedure is taking place;

extract image frames from the video feed displayed on the remote workstation display;

screen-scraping injector settings of the contrast injector from the image frames; and outputting an alert via an alert output device if the screen-scraped injector settings satisfy an alert criterion.

11. The non-transitory computer readable medium of claim 10, wherein the method includes:

retrieving a weight of a patient undergoing the contrast enhanced medical imaging procedure from a patient database;

wherein the alert criterion is based on the weight of the patient.

12. The non-transitory computer readable medium of claim 10, wherein the method includes:

retrieving an age of a patient undergoing the contrast enhanced medical imaging procedure from a patient database;

wherein the alert criterion is based on the age of the patient.

13. The non-transitory computer readable medium of claim 10, wherein the screen scraped injector settings include a screen scraped timed injection delay and the method includes:

retrieving temporal information related to the contrast enhanced medical imaging procedure from one or more guideline documents stored in a database based on the screen-scraped injection parameters;

wherein the alert criterion includes a criterion based on comparison of the screen-scraped timed injection delay and a range of temporal delay values in the retrieved documents.

14. The non-transitory computer readable medium of claim 10, wherein the screen scraped injector settings include a screen scraped contrast flow rate and the method includes:

retrieving a maximum contrast dose amount value from one or more guideline documents stored in a database;

wherein the alert criterion is based on comparison of the screen scraped contrast dose amount and the maximum dose amount.

15. The non-transitory computer readable medium of claim 10, wherein the method includes:

storing the screen-scraped injector settings annotated by an identification of the contrast enhanced medical imaging procedure in a database.

16. A method for providing remote assistance to a local operator of a medical imaging device including a contrast injector disposed in a medical imaging device bay, the method comprising:

providing a natural language communication link via to the medical imaging device bay via which a remote operator at a remote location that is remote from the medical imaging device bay provides remote assistance to the local operator at the medical imaging device bay;

receiving, from a camera disposed in the medical imaging device bay, a video stream including at least a display of the medical imaging device or of the contrast injector;

sharing the video stream of the medical imaging device or of the contrast injector at a remote workstation display disposed at the remote location and in direct communication with the camera, the display showing injector settings of the contrast injector;

extracting image frames from the video or screen sharing of the display of the medical device or contrast injector;

screen-scraping injector settings of the contrast injector from the image frames;

retrieving information on a contrast injection procedure from one or more databases based at least in part on the screen-scraped information; and displaying the screen-scraped injector settings and the retrieved information on the contrast injection procedure at the remote workstation display.

17. The method of claim 16, further including:

outputting an alert perceptible at the remote location when the screen-scraped information on the medical contrast injection procedure satisfies an alert criterion based at least one the retrieved information.

18. The method of claim 17, further including:

retrieving a weight or age of a patient undergoing the contrast enhanced medical imaging procedure from a patient database;

wherein the alert criterion is based on the weight or age of the patient.

19. The method of claim 17, wherein the screen scraped injector settings include a screen scraped timed injection delay and the method includes:

retrieving, from one or more guideline documents stored in a database, one of a temporal information related to the contrast enhanced medical imaging procedure or a maximum dose amount value based on the screen-scraped injection parameters;

wherein the alert criterion includes a criterion based on comparison of the screen-scraped timed injection delay and a range of temporal delay values in the retrieved documents or a comparison of the maximum dose amount value and the screen scraped dose amount value.

* * * * *